US00PP30511P3

(12) United States Plant Patent
Braun

(10) Patent No.: US PP30,511 P3
(45) Date of Patent: May 21, 2019

(54) APPLE TREE NAMED 'GALA 0502B'

(50) Latin Name: ***Malus domestica* Borkh**
Varietal Denomination: Gala 0502B

(71) Applicant: KIKU SRL GmbH, Girlan/Eppan (IT)

(72) Inventor: Jürgen Braun, Girlan/Eppan (IT)

(73) Assignee: KIKU SRL GmbH, Girlan/Eppan (IT)

( * ) Notice: Subject to any disclaimer, the term of this patent is extended or adjusted under 35 U.S.C. 154(b) by 0 days.

(21) Appl. No.: 15/732,045

(22) Filed: Sep. 8, 2017

(65) Prior Publication Data

US 2019/0082569 P1 Mar. 14, 2019

(51) Int. Cl.
*A01H 5/08* (2018.01)
*A01H 6/74* (2018.01)

(52) U.S. Cl.
USPC ..... Plt./162
CPC ..... *A01H 6/7418* (2018.05)

(58) Field of Classification Search
USPC ..... Plt./162
See application file for complete search history.

*Primary Examiner* — Susan McCormick Ewoldt
(74) *Attorney, Agent, or Firm* — Michelle Bos Legal LLC

(57) ABSTRACT

'Gala 0502B' apple is 'Gala' sport notable for its fruit, which attains a distinctive, deep purple-red color well before harvest. 'Gala 0502B' can be harvested in a single picking due to its early intense and even coloration.

5 Drawing Sheets

Latin name: *Malus domestica* Borkh.
Variety denomination: 'Gala 0502B'.

BACKGROUND OF THE VARIETY

'Gala 0502B' is a new and distinct variety of apple tree (*Malus domestica* Borkh), which variety originated as a limb sport mutation of 'Gala Royal Beaut' (not patented). 'Gala 0502B' was discovered by the inventor in a cultivated orchard at Casaleone, Verona, Italy in 2010, and was selected for further observation because of the distinctive early coloration of its fruit. 'Gala 0502B' was first asexually propagated by chip budding in 2011 at Presina, Italy, and has since been observed to remain true to type over successive asexually propagated generations.

BRIEF DESCRIPTION OF THE VARIETY

'Gala 0502B' was first selected for its distinctive fruit, which is fully colored well before harvest. Fruit of 'Gala 0502B' is also distinguished by its solid purple overcolor and its readiness for harvest in a single pick. The shoots, leaves, petioles, young fruit and fruit stem of 'Gala 0502B' are also notable for their darker color as compared to parent 'Gala Royal Beaut'. Table 1 sets forth a comparison of the fruit of 'Gala 0502B' to 'Gala Schnico' (U.S. Plant Pat. No. 27,577), 'Galaval' (U.S. Plant Pat. No. 19,909), 'Gala 0502' (U.S. Plant Pat. No. 28,235) and 'Gala'.

TABLE 1

Color Comparison of 'Gala 0502B' to Other 'Gala'-Type Varieties

| Variety | Color Characteristics |
|---|---|
| 'Gala 0502B' | Early homogeneous coloring, solid purple, no stripes |
| 'Gala Schnico' | Late non-homogeneous coloring, red solid flush with some stripes |
| 'Galaval' | Red solid flush with few stripes on backside of fruit |
| 'Gala 0502' | Early homogeneous coloring, red-purple, no stripes |
| 'Gala' | Bright red flush over pale yellow ground |

One hundred percent of the fruit of 'Gala 0502B' can be harvested in a single pick, as compared to about fifty percent to eighty percent of 'Gala Schnico'.

BRIEF DESCRIPTION OF THE PHOTOGRAPHS

Figure 1:
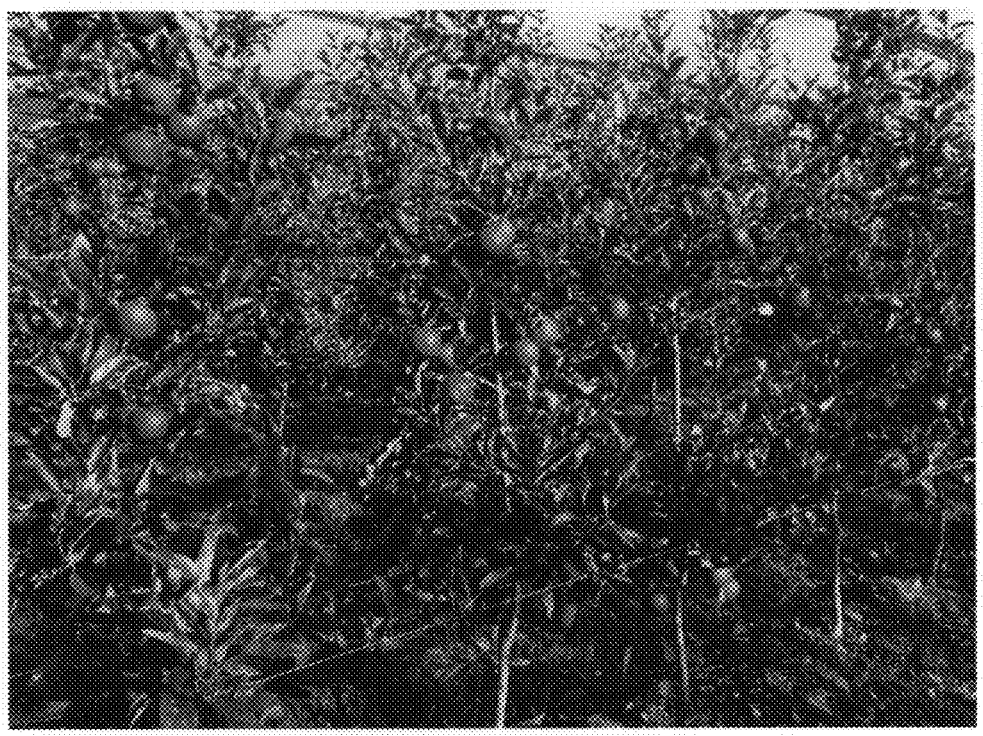
Figure 2:
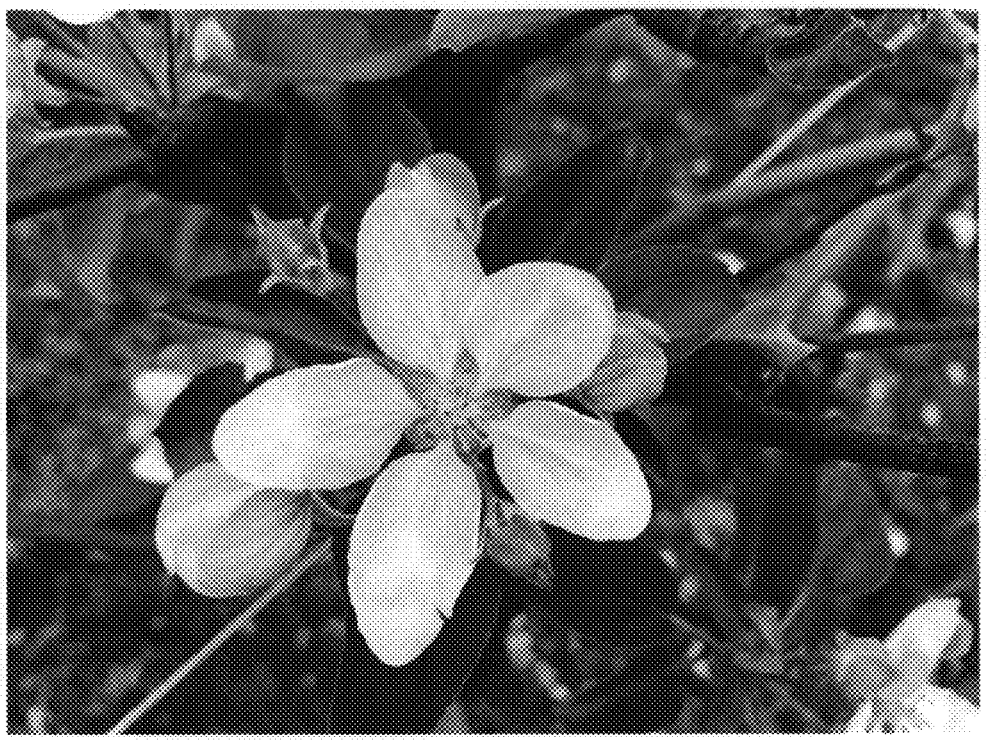
Figure 3:
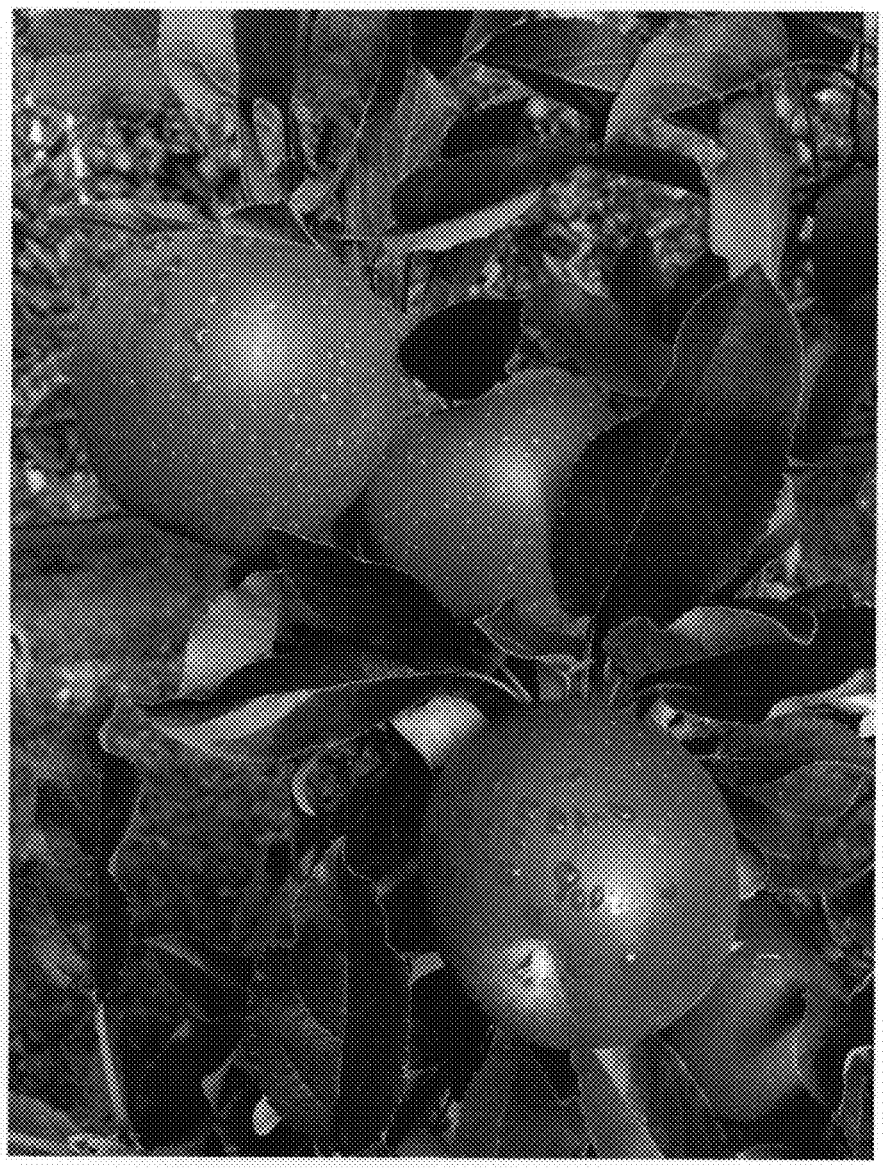
Figure 4:
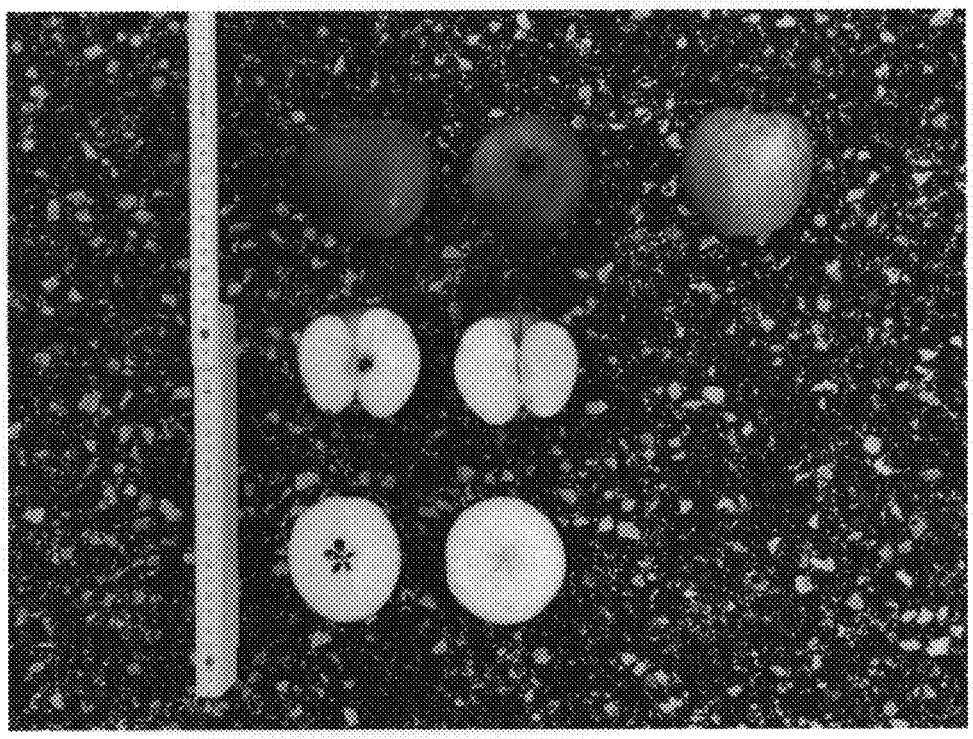
Figure 5:
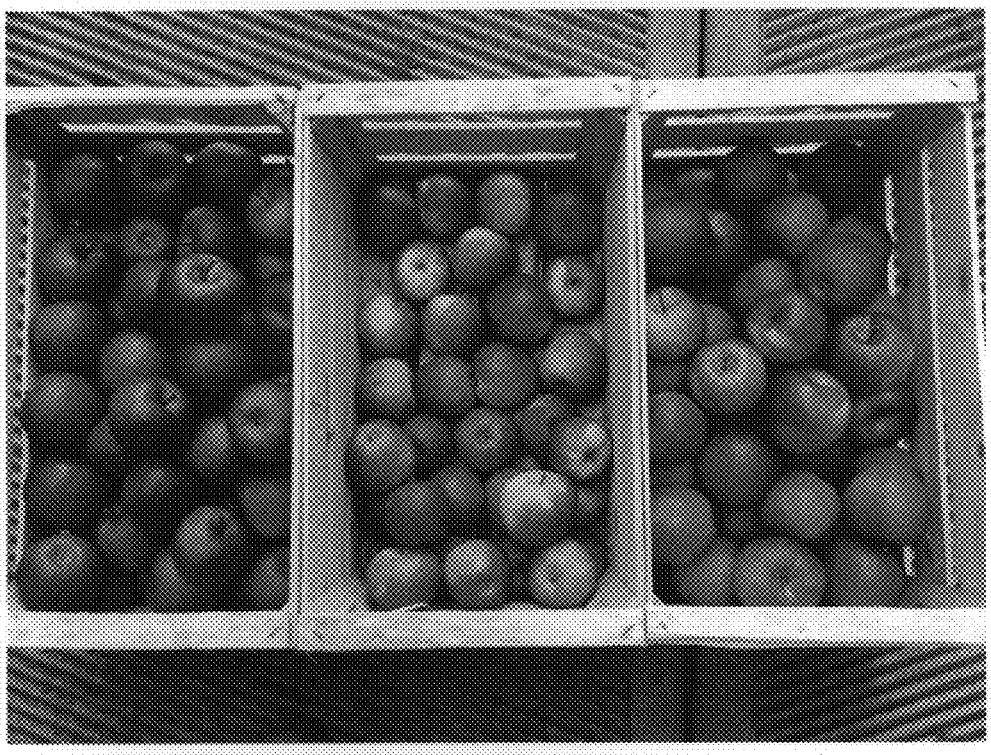

FIG. 1 shows trees of 'Gala 0502B';
FIG. 2 shows a flower of 'Gala 0502B';
FIG. 3 shows fruit and leaves on a 'Gala 0502B' tree;
FIG. 4 shows whole and sectioned fruit of 'Gala 0502B' (left and center) and 'Buckeye' (right); and
FIG. 5 shows fruit of 'Gala 0502B' (left), 'Buckeye' (center) and 'Galaval' (right)'.

Actual colors will vary with lighting conditions; color characteristics of 'Gala 0502B' apple tree should therefore be determined with reference to the observations described herein below, rather than from these illustrations alone.

DETAILED BOTANICAL DESCRIPTION OF THE VARIETY

The attached illustrations and the following detailed botanical description of 'Gala 0502B' apple tree are based on observations made and photos taken during the 2015 and 2016 growing seasons at Cornaiano, Italy of trees planted in 2013 on M9 T337 virus free rootstock (not patented). All colors are described according to The Royal Horticultural Society Colour Chart (2001). The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium (typical of 'Gala'-type varieties).
*Type*.—Ramified.
*Habit*.—Drooping.

*Trunk diameter* (*at* 30 *cm above the graft*).—2.5 cm+/−0.2 cm.
*Bark texture*.—Smooth.
*Bark color*.—Grey-brown 199A.
*Type of bearing*.—On spurs and long shoots.

Branch (fruiting branches located at around 1 m above the graft union):
*Length*.—70 to 100 cm.
*Diameter*.—1 cm+/−0.1 cm at 5 cm from the stem.
*Crotch angle*.—110 degrees+/−10 degrees.
*Bark color*.—Greyed-green 197A.
*Lenticel length*.—0.14 cm+/−0.05 cm.
*Lenticel color*.—Yellow-white 158A.
*Lenticels density*.—5+/−2 per $cm^2$.

One year old shoot:
*Length*.—50 cm+/−10 cm.
*Color*.—Greyed-purple 183A.
*Pubescence*.—Very weak.
*Thickness*.—0.5 cm+/−0.1 cm.
*Internode length*.—3.5 cm+/−0.5 cm.
*Lenticel density*.—12+/−2 per $cm^2$.

Flower buds:
*Quantity per spur*.—6 per spur.
*Shape*.—Oval.
*Length*.—0.6 cm.
*Diameter*.—0.4 cm.
*Color*.—Greyed-purple N187A.

Flowers:
*Diameter of fully open flower*.—5 cm+/−0.2 cm.
*Relative position of petal margin*.—Not touching.
*Number per cluster*.—5 plus king flower.
*Date of first bloom*.—April 10.
*Date of full bloom*.—April 17.
*Pollination requirement*.—Pollenizer required ('Fuji', 'Red Delicious', 'Granny Smith').

Petals (all measured on king flower):
*Number per flower*.—5.
*Shape*.—Oval.
*Length*.—2.4 cm+/−0.2 cm.
*Width*.—1.4 cm+/−0.2 cm.
*Apex*.—Round.
*Base*.—Pointed.
*Margin*.—Smooth.
*Color of upper surface*.—White NN155C with red 54C veins.
*Color of lower surface*.—White N155C with red 54B veins.

Stigma:
*Position*.—Above anthers (like 'Golden Delicious').
*Size*.—Diameter 0.08 cm+/−0.1 cm.
*Color*.—Yellow 5A.

Style:
*Size*.—Length 1.0 cm+/−0.1 cm.
*Color*.—Yellow-green 145A.

Ovary:
*Size*.—Length 0.5 cm+/−0.1 cm.
*Color*.—Yellow-green 144A.

Anthers:
*Quantity*.—10+/−2.
*Size*.—Length 0.7 cm+/−0.1 cm.
*Color*.—Yellow 10A.

Pedicel:
*Length*.—2.8 cm+/−0.2 cm.
*Diameter*.—0.1 cm+/−0.02 cm.
*Color*.—Yellow-green 145A.

Sepals:
*Quantity*.—5.
*Color*.—Green 142B.
*Shape*.—Pointed, triangular.
*Margin*.—Smooth.

Leaves:
*Shape*.—Elliptic.
*Length*.—Up to 12 cm.
*Width*.—Up to 5 cm.
*Blade margin*.—Serrate.
*Apex*.—Acute.
*Base shape*.—Rounded.
*Division*.—Simple.
*Arrangement*.—Alternate.
*Venation*.—Pinnate.
*Vein color*.—Upper surface green 139C; lower surface red-purple 59A at base, fading to green 139D at apex.
*Color of upper surface*.—Green 139A.
*Color of lower surface*.—Green 139C.
*Attitude in relation to shoot*.—Outward.

Petiole:
*Length*.—4.3 cm+/−0.2 cm.
*Diameter*.—1.5 mm+/−0.1 mm.
*Color of upper surface*.—Red-purple 59A.
*Color of lower surface*.—Red-purple 59A.

Fruit:
*Quantity per cluster*.—Up to 5.
*Diameter*.—77 mm+/−7 mm.
*Weight*.—210 g+/−30 g.
*General shape in profile*.—Conic.
*Position of maximum diameter*.—Upper 50% in profile.
*Ribbing*.—Absent or weak.
*Crowning at calyx end*.—Moderate.
*Aperture of eye*.—Closed.
*Length of sepal*.—Long, 0.5 cm+/−0.1 cm.
*Bloom of skin*.—Medium.
*Greasiness of skin*.—Absent.
*Background color of skin*.—Not visible.
*Amount of over color*.—100%.
*Over color of skin*.—Purple N79B.
*Intensity of over color*.—High.
*Pattern of over color*.—Solid flush.
*Amount of russet around stalk cavity*.—Absent or small.
*Amount of russet on cheeks*.—Absent.
*Area of russet around eye basin*.—Absent.
*Length of stalk*.—2.1 cm+/−0.2 cm.
*Thickness of stalk*.—0.3 cm+/−0.1 cm.
*Depth of stalk cavity*.—1.4 cm+/−0.2 cm.
*Width of stalk cavity*.—1.6 cm+/−0.2 cm.
*Depth of eye basin*.—Shallow, 0.7 cm to 1 cm deep.
*Width of eye basin*.—2.3 cm+/−0.2 cm.
*Firmness of flesh*.—Medium, 6.5 kg per $cm^2$.
*Flesh texture*.—Crisp.
*Aroma*.—Sweet.
*Juiciness*.—High.
*Brix*.—14 to 15 ° Brix.
*Flesh color*.—Yellow 10D.
*Number of lenticels*.—5+/−2 per $cm^2$.
*Size of lenticels*.—Large, up to 3 mm diameter.
*Aperture of locules*.—Moderately open.
*Stem color*.—Brown 200B.

Seeds:

*Quantity per fruit*.—Up to 2 per chamber, up to 10 per fruit.

*Shape*.—Pointed.

*Length*.—0.8 cm+/−0.1 cm.

*Breadth*.—0.45 cm+/−0.1 cm.

*Color*.—Greyed-orange 177A.

Harvest:

*Time for harvest*.—Mid-August, similar to other mid-season 'Gala' varieties.

*Number of picks*.—1.

*Amount of fruit produced per tree per harvest*.—20 kg+/−2 kg.

*Disease resistance/susceptibility*.—None noted; same as other 'Gala' varieties.

*Market use*.—Fresh.

*Storageability*.—Up to 9 months in controlled atmosphere storage.

I claim:

1. A new and distinct apple tree, substantially as described and illustrated herein.

* * * * *